United States Patent
Chamberlain et al.

(10) Patent No.: US 11,202,923 B2
(45) Date of Patent: Dec. 21, 2021

(54) MOBILE RADIATION ONCOLOGY COACH SYSTEM WITH INTERNAL AND/OR EXTERNAL SHIELDING FOR SAME

(71) Applicant: Alliance Oncology, LLC, Irvine, CA (US)

(72) Inventors: David Chamberlain, Reno, NV (US); Brent Murphy, South Bend, IN (US); Harry Freeman, Mission Viejo, CA (US)

(73) Assignee: Alliance Oncology, LLC, Irvine, CA (US)

( * ) Notice: Subject to any disclaimer, the term of this patent is extended or adjusted under 35 U.S.C. 154(b) by 0 days.

(21) Appl. No.: 16/802,402

(22) Filed: Feb. 26, 2020

(65) Prior Publication Data

US 2020/0188693 A1 Jun. 18, 2020

Related U.S. Application Data

(63) Continuation of application No. 16/688,979, filed on Nov. 19, 2019, now Pat. No. 11,000,699.
(Continued)

(51) Int. Cl.
| | |
|---|---|
| *A61N 5/10* | (2006.01) |
| *B60P 3/00* | (2006.01) |
| *B60P 3/34* | (2006.01) |
| *B60P 3/36* | (2006.01) |
| *G21F 3/04* | (2006.01) |
| *G21F 7/00* | (2006.01) |
| *G21F 7/005* | (2006.01) |

(52) U.S. Cl.
CPC .............. *A61N 5/1048* (2013.01); *B60P 3/00* (2013.01); *B60P 3/34* (2013.01); *B60P 3/36* (2013.01); *G21F 3/04* (2013.01); *G21F 7/00* (2013.01); *G21F 7/005* (2013.01); *A61N 5/1077* (2013.01); *A61N 2005/1074* (2013.01); *A61N 2005/1094* (2013.01)

(58) Field of Classification Search
CPC .......... A61N 5/1048; A61N 2005/1074; A61N 2005/1094; B60P 3/00
See application file for complete search history.

(56) References Cited

U.S. PATENT DOCUMENTS

| | | |
|---|---|---|
| 5,727,353 A | 3/1998 | Getz et al. |
| 2005/0166473 A1 | 8/2005 | Jorg |

(Continued)

OTHER PUBLICATIONS

International Search Report issued to PCT Application No. PCT/US2020/014175 dated May 18, 2020.
(Continued)

*Primary Examiner* — Nicole M Ippolito
*Assistant Examiner* — Hanway Chang
(74) *Attorney, Agent, or Firm* — Manatt, Phelps & Phillips, LLP

(57) ABSTRACT

A mobile radiation oncology coach system is disclosed. The mobile radiation oncology coach system comprise a trailer having a control console area and a treatment area, the treatment area is equipped with a medical treatment facility. The mobile radiation oncology coach system further comprise an internal shielding provided between the control console area and the treatment area. The mobile radiation oncology coach system further comprise an external shielding provided at the outside of the trailer.

32 Claims, 15 Drawing Sheets

Related U.S. Application Data

(60) Provisional application No. 62/770,125, filed on Nov. 20, 2018.

(56) References Cited

U.S. PATENT DOCUMENTS

| | | |
|---|---|---|
| 2007/0164238 A1* | 7/2007 | Pomper .................... B60P 3/14 250/493.1 |
| 2007/0269008 A1* | 11/2007 | Pomper ................. A61G 3/001 378/65 |
| 2008/0203331 A1 | 8/2008 | Murphy |
| 2009/0175414 A1 | 7/2009 | Messinger |
| 2012/0159849 A1 | 6/2012 | Farrell |
| 2012/0207276 A1 | 8/2012 | Pomper |
| 2013/0082196 A1 | 4/2013 | Farrell |
| 2015/0101275 A1 | 4/2015 | Lefkus, III et al. |
| 2018/0110666 A1 | 4/2018 | Yim et al. |
| 2018/0258659 A1 | 9/2018 | LeBlanc et al. |

OTHER PUBLICATIONS

Written Opinion issued to PCT Application No. PCT/US2020/014175 dated May 18, 2020.

* cited by examiner

| BARRIER | SHIELDING (INCHES SB240) T=0.5 | SHIELDING (INCHES SB240) T=1.0 |
|---|---|---|
| 201 | 24 | 28 |
| 202 | 22 | 25 |
| 203 | 22 | 25 |
| 204 | 22 | 25 |
| 205 | 24 | 28 |
| 206 | 22 | 25 |
| 207 | 22 | 25 |
| 208 | 22 | 25 |
| 209 | 22 | 25 |
| 210 | 12 | 14 |
| 211 | 6 | 7 |

FIG. 11

MOBILE RADIATION ONCOLOGY COACH SYSTEM WITH INTERNAL AND/OR EXTERNAL SHIELDING FOR SAME

INCORPORATION BY REFERENCE TO RELATED APPLICATIONS

This application is a continuation of U.S. application Ser. No. 16/688,979, filed on Nov. 19, 2019, which claims the benefit of, and priority to, U.S. Provisional Application No. 62/770,125, filed on Nov. 20, 2018. All of the above applications are hereby incorporated herein by reference in their entirety.

BACKGROUND

Field

This disclosure relates generally to mobile radiation oncology coach system and more specifically to a mobile radiation oncology coach system with internal and/or external shielding to a mobile unit.

Description of the Related Art

A medical linear particle accelerator (LINAC) is widely used to treat cancer by using customized high energy x-rays or electrons to conform to a tumor's shape of a patient and destroy cancer cells while sparing surrounding normal tissue of the patient. Like all expensive equipment, a LINAC with normal usage (e.g., 25 treatments per day) would require regular maintenances in addition to daily or weekly-based calibrations. Typically, a regular maintenance would require the LINAC to be shut down for a period of time that may takes weeks or months. In addition, when an upgrade for renovation or when new equipment installation is required, the LINAC is typically shut down. The shutdown of a single vault LINAC facility could cost a million dollars of revenue lost during a multi-month shutdown.

The inventors here have recognized that there is a need for mobile and/or interim (e.g., portable, substantially portable/movable, leasing) radiation oncology service solutions that are capable of overcoming the foregoing shortcomings and maintain high-quality care, referrals and revenue while the fixed site equipment is temporarily unavailable or where fixed site equipment are not possible.

SUMMARY

Disclosed here are numerous aspects of a unique and advantageous mobile radiation oncology coach equipped with state-of-the-art LINAC facility that is able to provide the same or equivalent technology, such as accelerated treatment times, a six-point safety system, ergonomic operator controls and many patient-friendly features, that are typically offered to patients in leading cancer centers. While patients receive excellent clinical care, the user and/or owners of the mobile radiation oncology coach experience no disruption in referrals, revenue or staffing during equipment upgrades or construction projects.

In some embodiments, a mobile radiation oncology coach system comprises a trailer configured to include a control console area, a treatment area, and a vestibule area located between the control console area and the treatment area, the treatment area being equipped with a medical treatment facility that can emit radiation; a first internal shielding provided between the vestibule area and the treatment area; a first door configured and providing access between the treatment area and the vestibule area, the first door including a first supplemental shielding; and a second door configured and providing access between the vestibule area and the control console area, the second door including second supplemental shielding and further configured to be constructed near an opposite side of said trailer, preventing a direct line of sight between the treatment area and the control console area.

In some embodiments, the first internal shielding comprises interlocked lead bricks. In some embodiments, the interlocked lead bricks comprises a predetermined thickness to provide substantially effective shielding between the control console area and the treatment area. In some embodiments, the mobile radiation oncology coach system further comprises a second internal shielding provided between the vestibule area and the control console area. In some embodiments, the second internal shielding comprises additional interlocked lead bricks comprising a second thickness to provide substantially effective shielding between the control console area and the vestibule area. In some embodiments, the mobile radiation oncology coach system further comprises an alternating door containing interlocked lead bricks to shield direct line of sight of the medical treatment facility and people located in the control console area. In some embodiments, the medical treatment facility includes medical linear particle accelerator (LINAC). In some embodiments, the mobile radiation oncology coach system further comprises an external shielding, wherein the external shielding comprising a plurality of barriers. In some embodiments, the plurality of barriers are made of concrete. In some embodiments, the mobile radiation oncology coach system further comprises a support pad dimensioned to support the trailer, and wherein the support pad comprises concrete. In some embodiments, the mobile radiation oncology coach system further comprises a tractor, wherein said tractor and said trailer are arranged in tandem. In some embodiments, the first door is a pocket door that is driven by a motor which in turn is controlled by door switches. In some embodiments, the mobile radiation oncology coach system further comprises a lever for manually disengaging the pocket door and the motor.

In some embodiments, a mobile radiation oncology coach system comprises a trailer configured to include a control console area and a treatment area, the treatment area being equipped with a medical treatment facility that can emit radiation; a first internal shielding disposed between the control console area and the treatment area; a first door configured and providing access between the treatment area and the control console area, the first door including a first supplemental shielding, wherein the first door is further configured to be constructed and positioned to prevent a direct line of sight between the treatment area and the control console area; and a swing door including second supplemental shielding, and constructed and positioned to shield radiation that may be emitted in an area associated with the first door between the treatment area and the control console area.

In some embodiments, the first internal shielding comprises interlocked lead bricks. In some embodiments, the interlocked lead bricks comprises a predetermined thickness to provide substantially effective shielding between the control console area and the treatment area. In some embodiments, the mobile radiation oncology coach system further comprises a vestibule area located between the control console area and the treatment room; and a second internal shielding provided between the vestibule area and the control console area. In some embodiments, the second internal shielding comprises additional interlocked lead bricks comprising a second thickness to provide substantially effective shielding between the control console area and the vestibule area. In some embodiments, the medical treatment facility includes medical linear particle accelerator (LINAC). In some embodiments, the mobile radiation oncology coach system further comprises an external shielding, wherein the external shielding comprising a plurality of barriers. In some embodiments, the plurality of barriers are made of concrete. In some embodiments, the mobile radiation oncology coach system further comprises a support pad dimensioned to support the trailer, and wherein the support pad comprises concrete.

In some embodiments, a mobile radiation oncology coach system comprises a trailer configured to include a control console area and a treatment area, the treatment area being equipped with a medical treatment facility that can emit radiation; internal shielding disposed between the control console area and the treatment area; and external shielding provided at a predetermined location outside of the trailer.

In some embodiments, the internal shielding comprises interlocked lead bricks. In some embodiments, the interlocked lead bricks comprises a predetermined thickness to provide substantially effective shielding between the control console area and the treatment area. In some embodiments, the mobile radiation oncology coach system further comprises a vestibule area located between the control console area and the treatment room; and a second internal shielding provided between the vestibule area and the control console area. In some embodiments, the second internal shielding comprises additional interlocked lead bricks comprising a second thickness to provide substantially effective shielding between the control console area and the vestibule area. In some embodiments, the mobile radiation oncology coach system further comprises an alternating door between the treatment room and the control console area, wherein the alternating door contains interlocked lead bricks to shield direct line of sight of the medical treatment facility and people located in the control console area. In some embodiments, the mobile radiation oncology coach system further comprises a first door configured and providing access between the treatment area and the vestibule area, the first door including first shielding; and a second door configured and providing access between the vestibule area and the control console area, the second door is further configured to be constructed near an opposite side of said trailer, preventing a direct line of sight between the treatment area and the control console area. In some embodiments, the mobile radiation oncology coach system further comprises a first door configured and providing access between the treatment area and the control console area, the first door including first supplemental shielding. In some embodiments, the first door is further configured to be constructed and positioned to prevent a direct line of sight between the treatment area and the control console area. In some embodiments, the mobile radiation oncology coach system further comprises a swing door including a second supplemental shielding, and constructed and positioned to shield radiation that may be emitted in an area associated with the first door between the treatment area and the control console area. In some embodiments, the medical treatment facility includes medical linear particle accelerator (LINAC). In some embodiments, the external shielding comprising a plurality of barriers. In some embodiments, the plurality of barriers are made of concrete. In some embodiments, the mobile radiation oncology coach system further comprises a support pad dimensioned to support the trailer, and wherein the support pad comprises concrete. In some embodiments, the mobile radiation oncology coach system further comprises a tractor, and wherein said tractor and said trailer are arranged in tandem.

In some embodiments, a method for providing a mobile radiation oncology services, the method comprises moving a trailer to a designated site, the trailer having a control console area and a treatment area being equipped with a medical treatment facility that can emit radiation; providing an internal shielding disposed between the control console area and the treatment area; and providing an external shielding at a predetermined location outside of the trailer.

In some embodiments, the internal shielding comprising interlocked lead bricks. In some embodiments, the method further comprises providing an alternating door positioned between the treatment area and the control console area, wherein the alternating door contains interlocked lead bricks to take away direct line of sight of the medical treatment facility and people located in the control console area. In some embodiments, the medical treatment facility is a LINAC. In some embodiments, the external shielding comprising a plurality of barriers. In some embodiments, the plurality of barriers is made of concrete. In some embodiments, the method further comprises providing a support pad dimensioned to support the trailer, wherein the support pad is made of concrete. In some embodiments, the method further comprises providing a tractor, wherein the tractor and the trailer are arranged in tandem. In some embodiments, the method further comprises securing the trailer after the trailer is moved to the designated site. In some embodiments, the method further comprises removing the external shielding after the services is complete.

It should be understood that each of the foregoing and various aspects, together with those set forth in the claims and summarized above and/or otherwise disclosed herein, including the drawings, may be combined to support claims for a device, apparatus, system, method of manufacture, and/or use without limitation.

BRIEF DESCRIPTION OF THE DRAWINGS

These and other features, aspects and advantages are described below with reference to the drawings, which are intended to illustrate, but not to limit, the invention. In the drawings, like reference characters denote corresponding features consistently throughout similar embodiments.

FIG. 11 is table showing shielding for external shielding barriers identified in FIG. 10 according to some embodiments.

DETAILED DESCRIPTION OF THE PREFERRED EMBODIMENT

Figure 1:
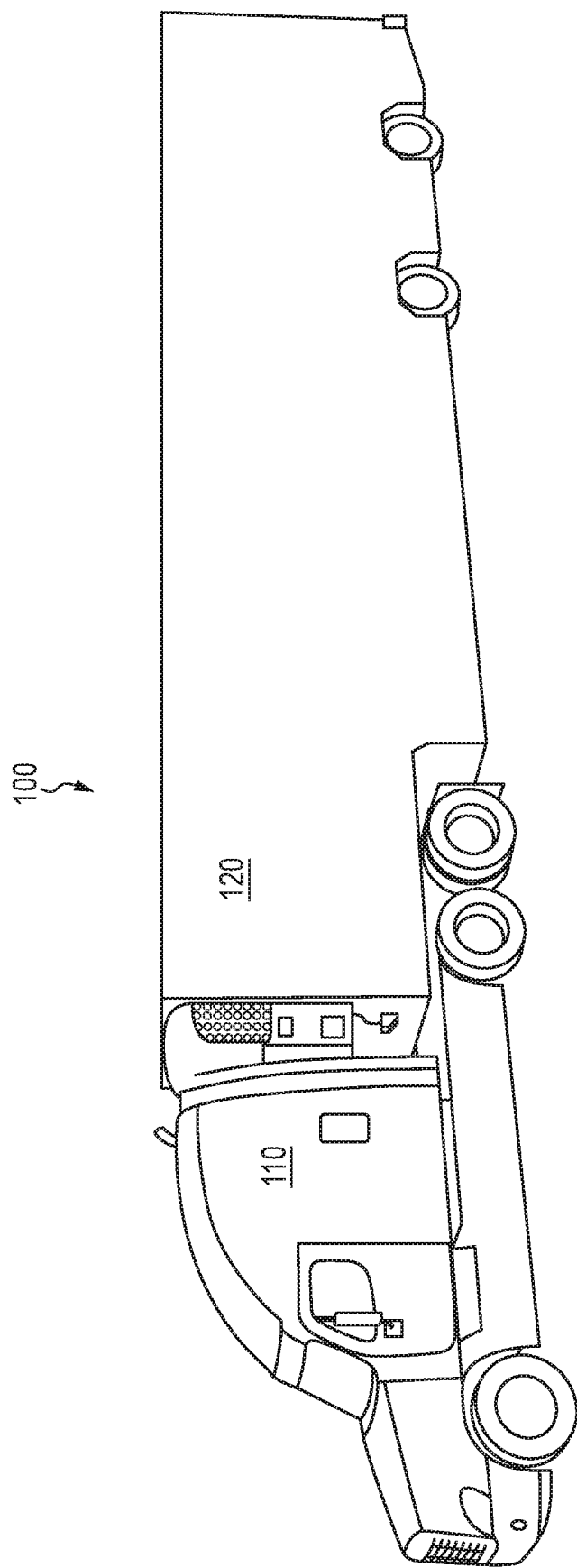
FIG. 1 depicts a front-right perspective view of a mobile unit of an exemplary mobile radiation oncology coach system in accordance with some embodiments. The exemplary mobile unit has a tractor and a trailer arranged in tandem.

As summarized above and illustrated in the drawings, disclosed herein are various aspects and embodiments of a mobile radiation oncology coach system.

According to some embodiments, the exemplary mobile radiation oncology coach system 10 described herein comprises a mobile unit 100, an external shielding 201-211 and an optional support pad 300. Referring to FIG. 1, the mobile unit 100 has a tractor 110 and a trailer or relocatable coach 120 arranged in tandem.

The trailer 120 can be attached to the tractor 110 during relocation (travel mode). The trailer 120 is configured to house a LINAC facility. When the trailer 120 is in the treatment configuration or clinical mode, the trailer 120 can be detached from the tractor 110 so that the tractor 110 can be separated from the trailer 120 for other duties. In some embodiments, the mobile unit 100 can be a single motorized vehicle (e.g., a bus or a motorhome) instead of a separate tractor and trailer combination.

In the exemplary embodiment, the mobile trailer 120 is about 58 feet in length and about 13 feet 6 inches in height. When the mobile trailer 120 is in the travel mode, the mobile trailer 120 is about 10 feet in width. In the exemplary embodiment, the mobile trailer 120 has slide-out sections that allow the width of the mobile trailer 120 to be extended to a wingspan of about 18 feet in width when the mobile unit 100 is in the clinical mode. In some embodiments, the dimensions of the mobile trailer 120 are varied, including the dimensions of the slide-out sections.

Preferably, the mobile trailer 120 is provided with sufficient area to be maneuvered and positioned for setup and takedown. The mobile trailer 120 can be provided with external storage compartments and service doors that require access during processes or operation. The slide-out sections, patient lift, entry stair and any optional platform may require additional space on the passenger side of the mobile unit 100. In some embodiments, storage compartments, service doors, slide out sections, patient lift and/or platforms are provided in alternative configurations.

Figure 2:
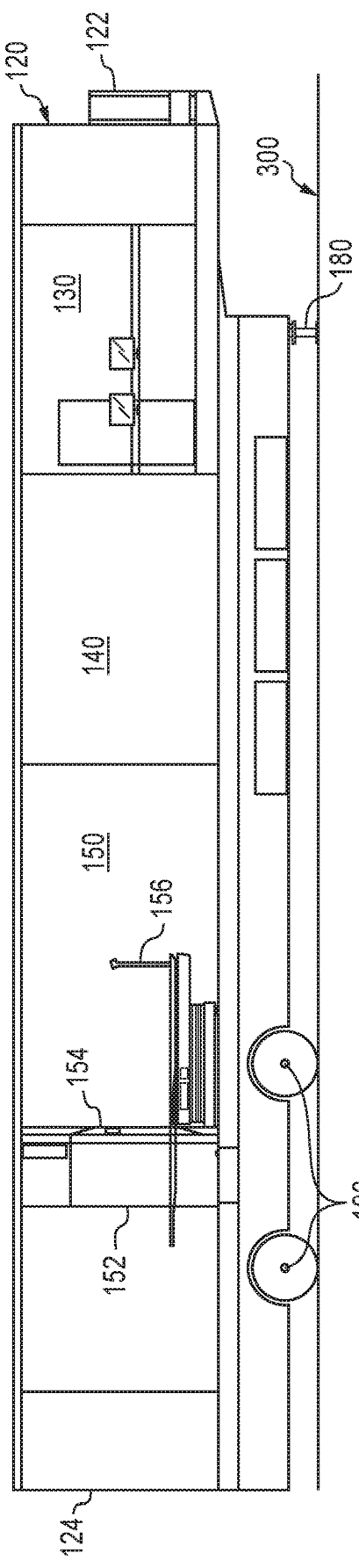
FIG. 2 is a left side elevational view of the trailer of the mobile unit illustrated in FIG. 1.

Referring also to FIG. 2, proper and safe operation of the LINAC system can be obtained when the mobile trailer 120 is located on a substantially level area or firm pad 300. Hydraulic support legs 180 can be provided to assist in the leveling and stabilization of the mobile trailer 120. In some embodiments, load bearing screw jacks and support legs can ultimately replace the hydraulic support legs as long-term support. In some embodiments, the recommended mobile unit support pad 300 is a concrete pad with a dimension of, for example, 20 feet wide and 60 feet long.

In some embodiments, the minimum support pad 300 could be split into two or more separate pads, rather than one large pad if properly configured. For example, a support pad 300 at the front 122 of the mobile trailer 120 can provide support for the landing gear, leveling legs and king pin support. A support pad at the rear 124 of the mobile trailer 120 can support tandem-axles (two sets of axles) 190, the hydraulic leveling legs and the load bearing screw jacks.

Figure 12:
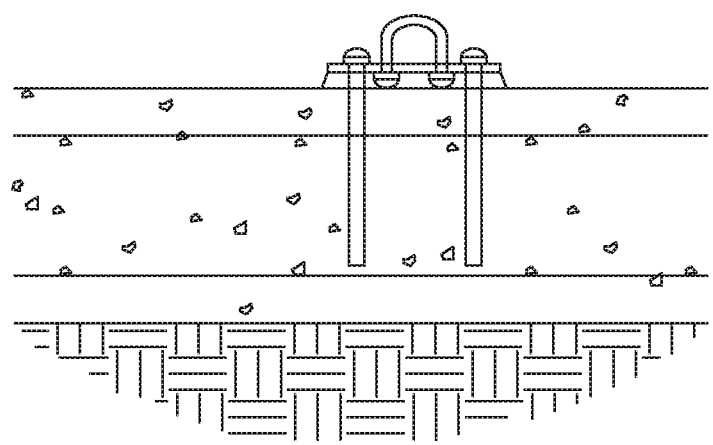
FIG. 12 depicts a typical pad layout and typical tie down.
Figure 13:
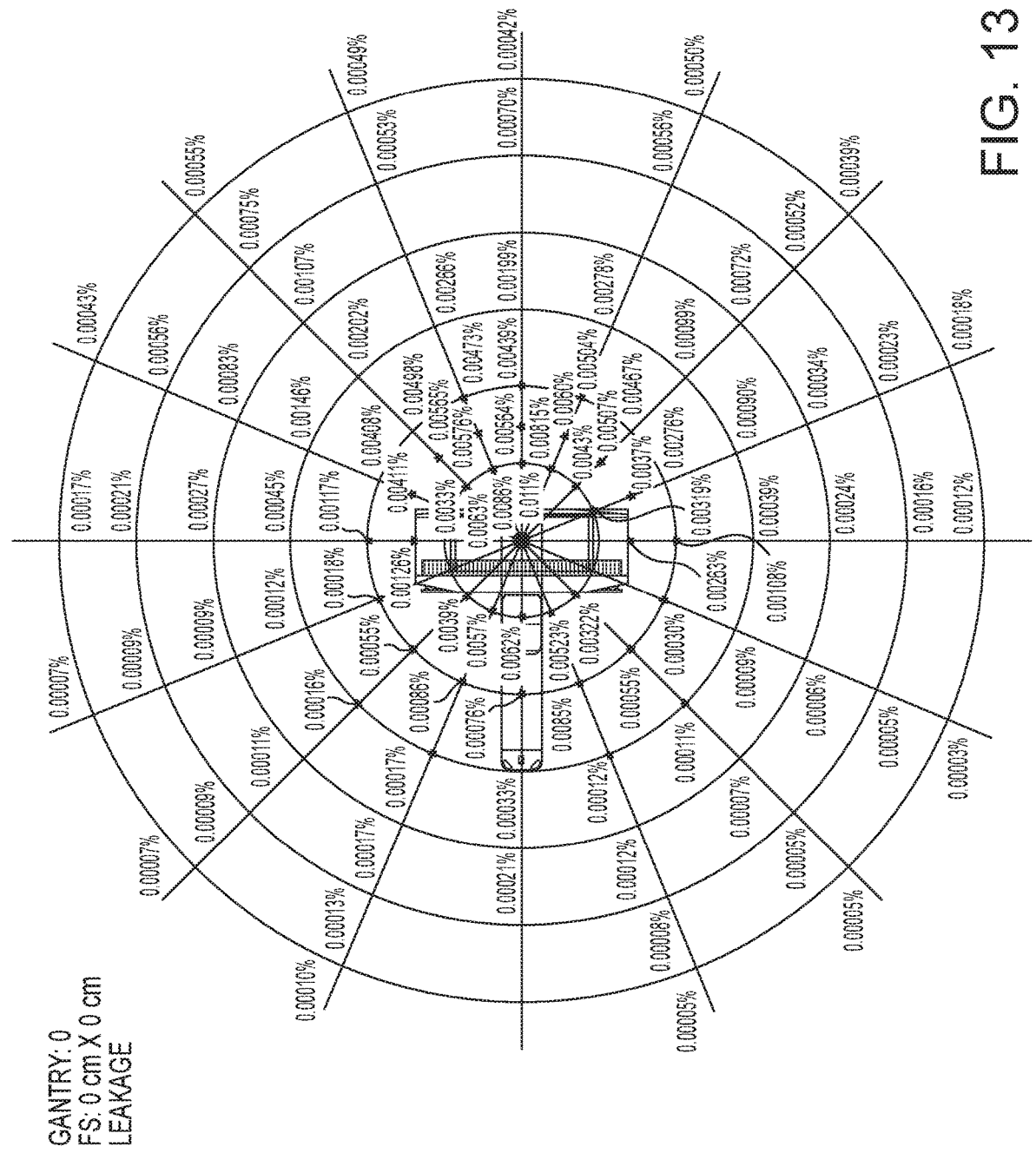
FIGS. 13-18 depict diagrams of radiation scatter and leakage measurements conducted on the exemplary mobile unit of FIG. 1.
Figure 14:
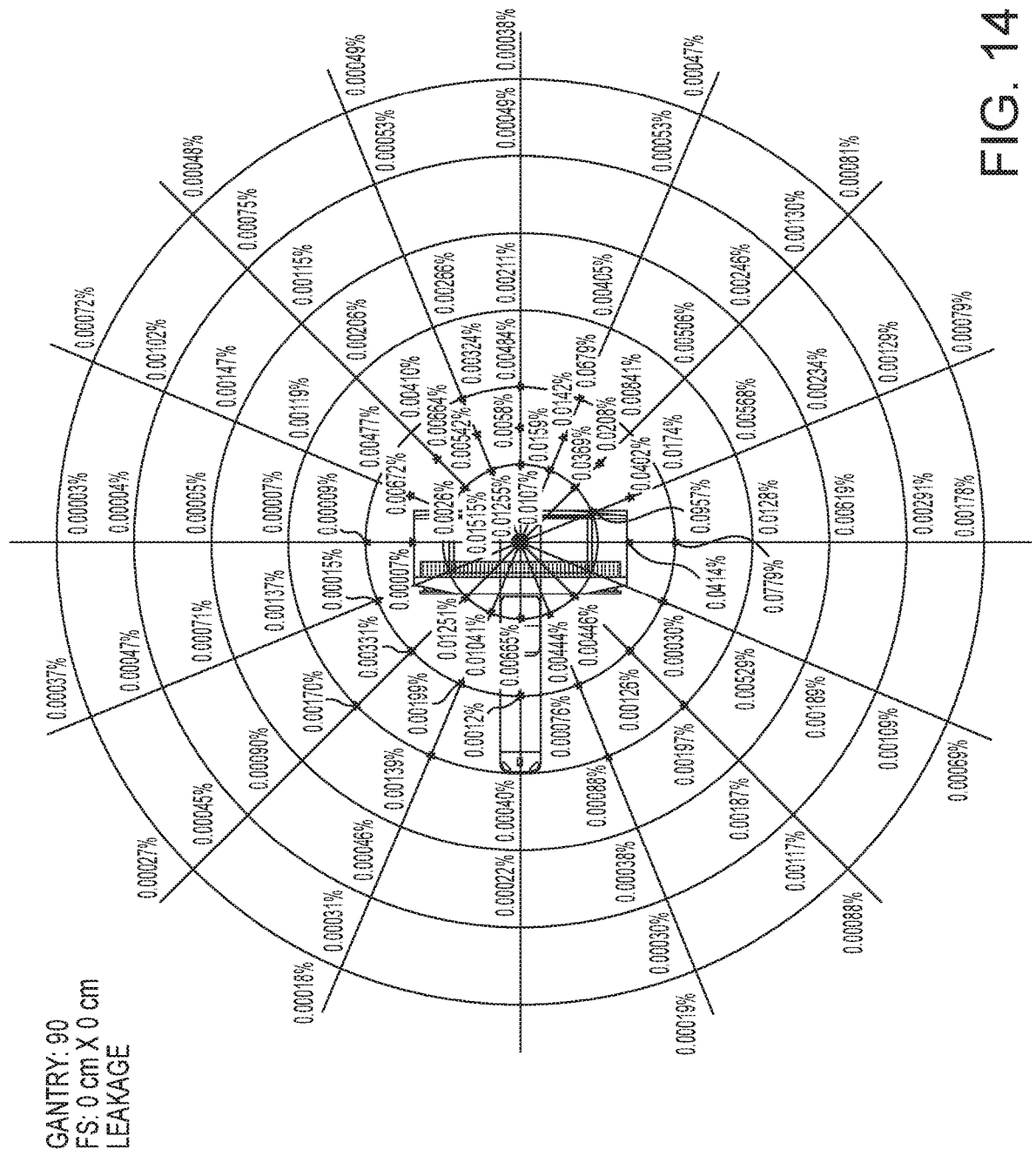
Figure 15:
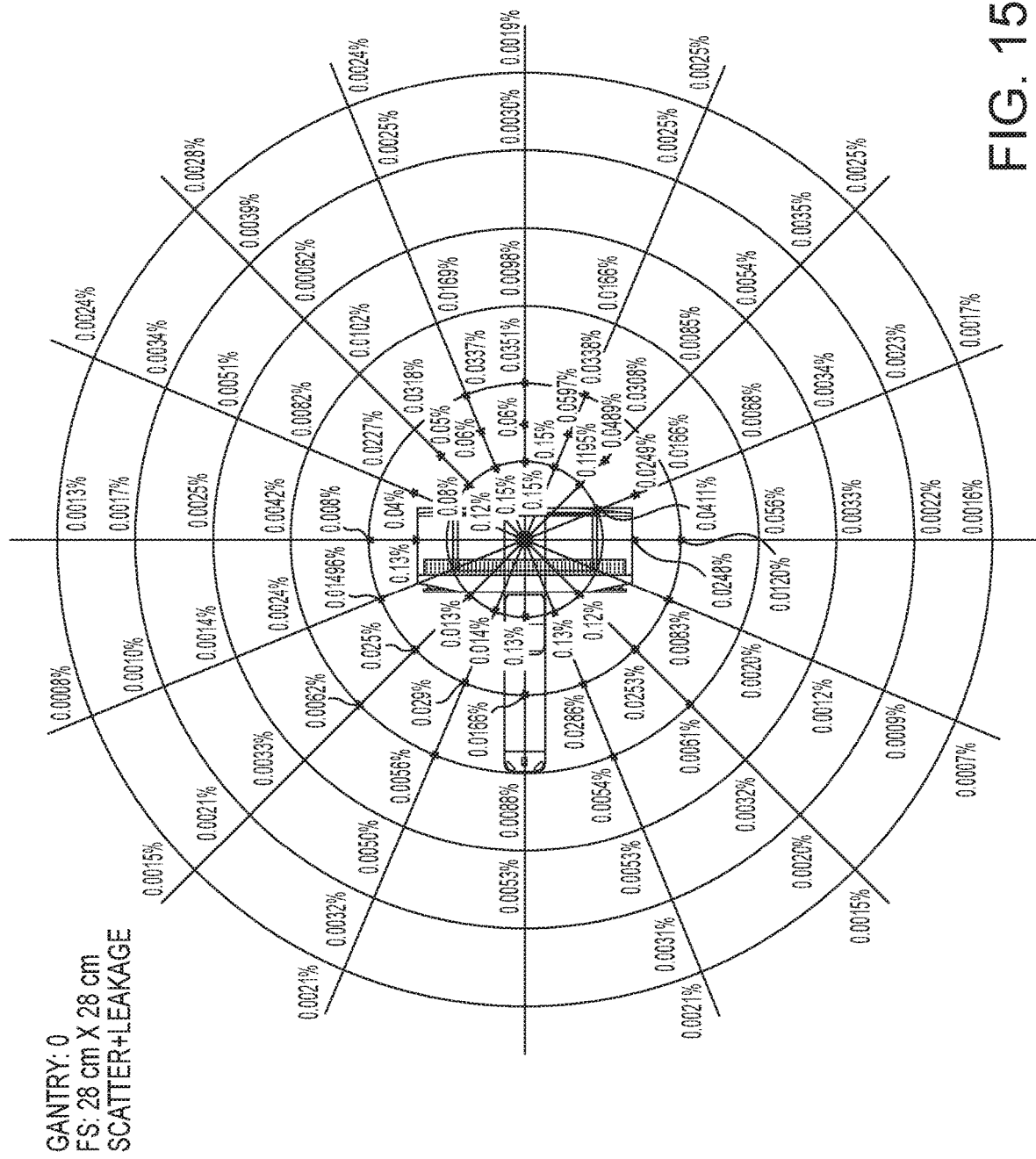
Figure 16:
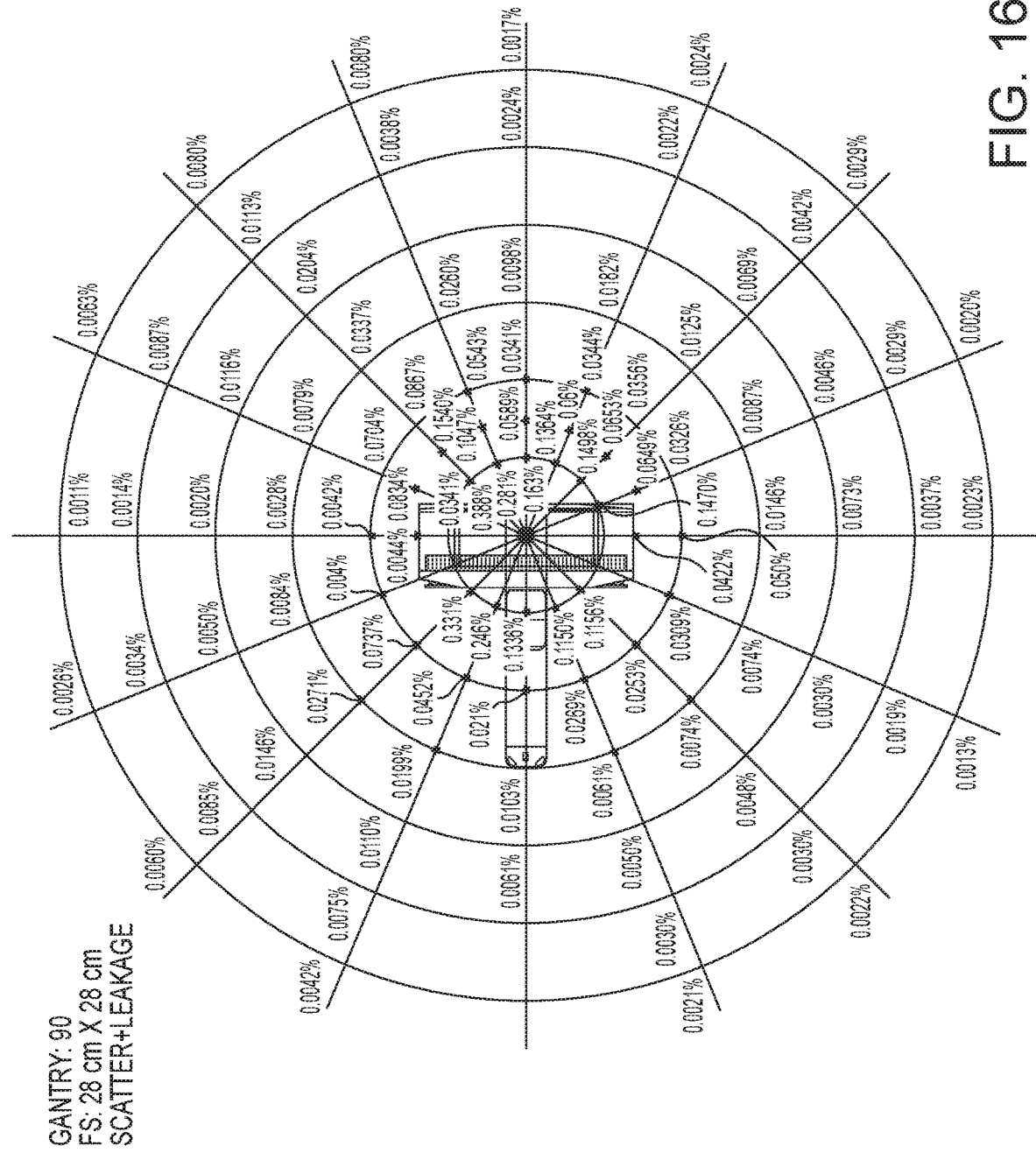
Figure 17:
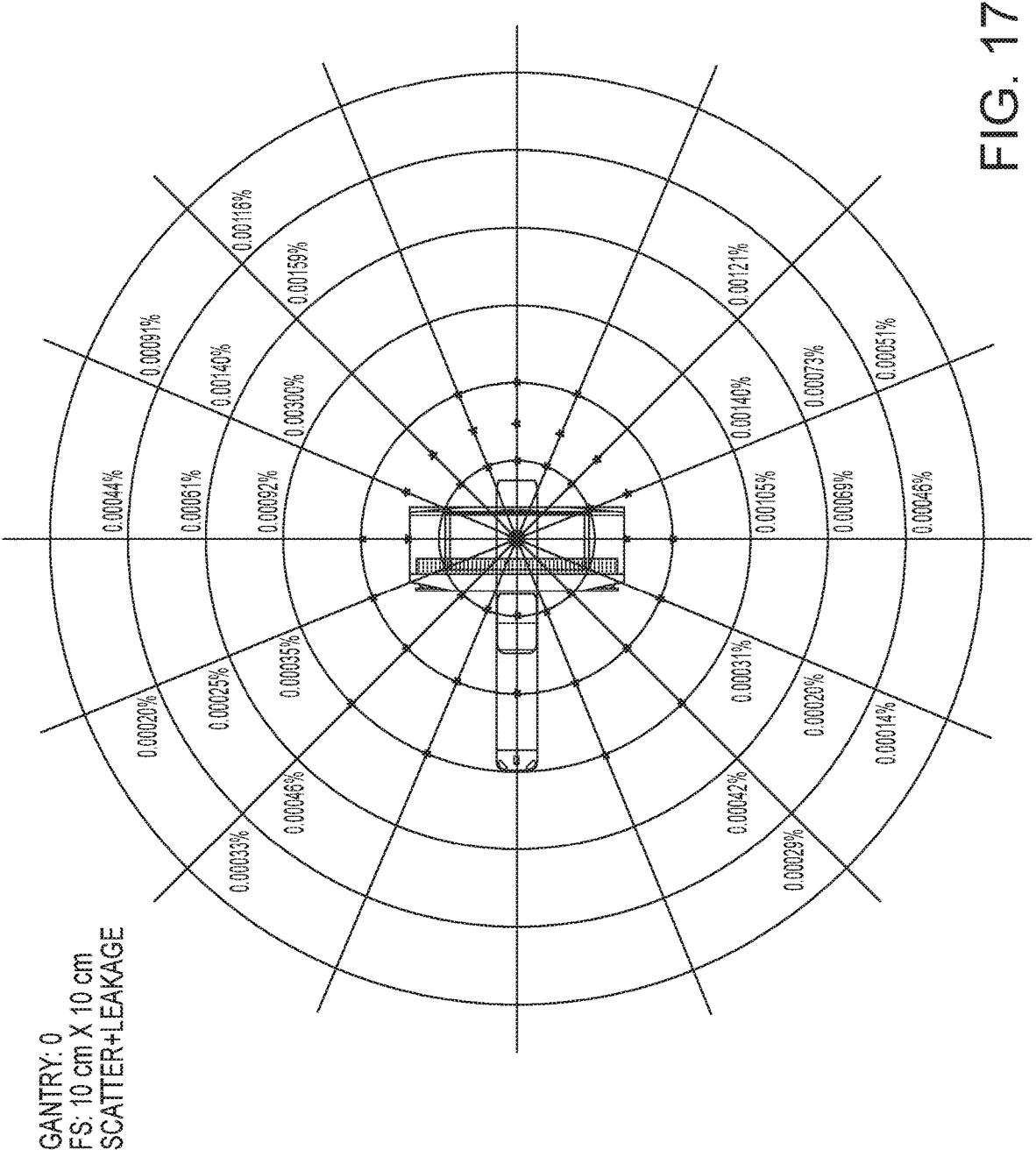
Figure 18:
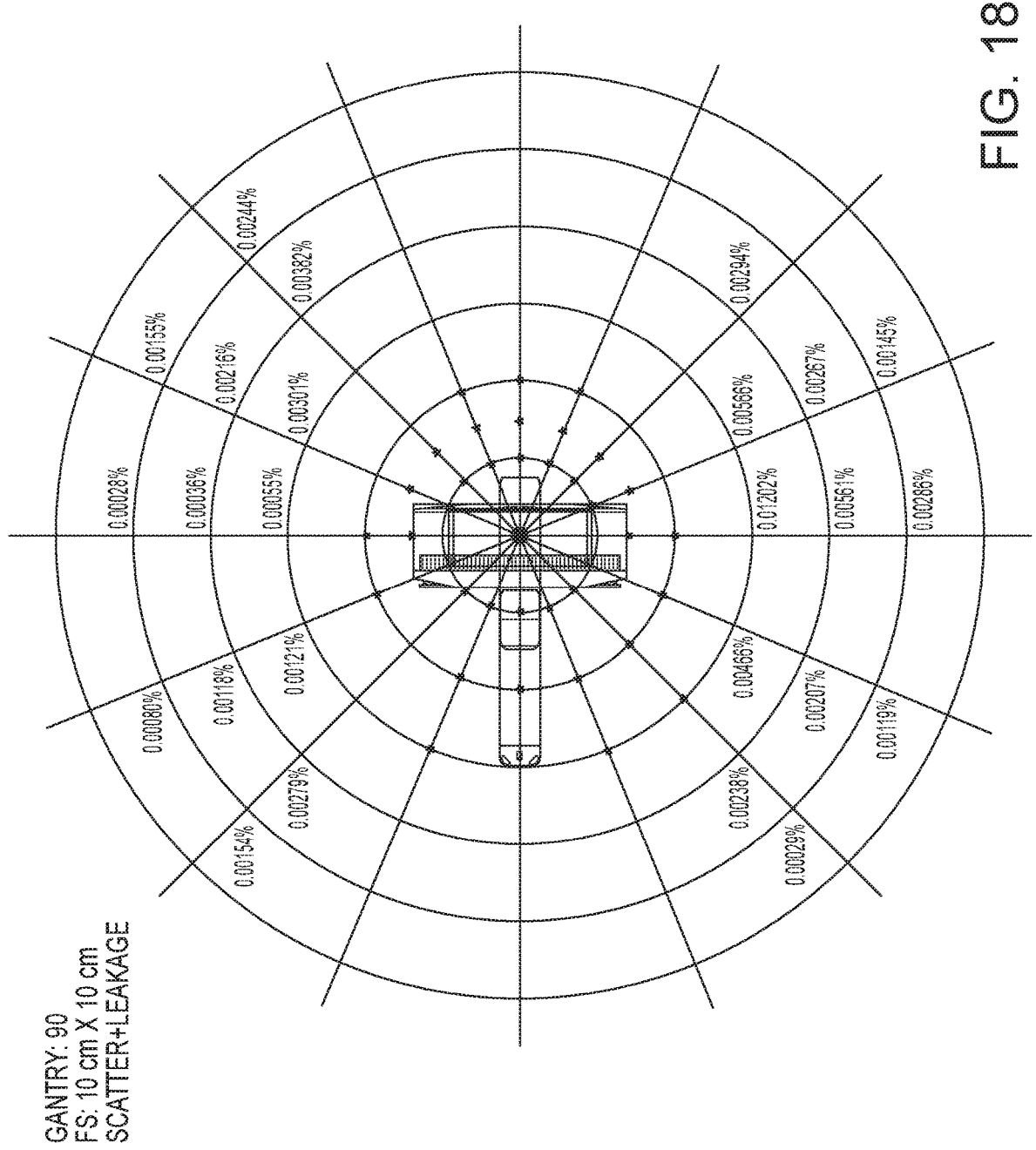

Referring also to FIG. 12, in some embodiments, the thickness of support pad 300 is to be determined at the local level, based on, for example, soil conditions. In some embodiments, the levelness of support pad 300 is preferably not to exceed ¼ inches per 10 feet.

In some embodiments, the overall length of the mobile unit 100 of the tractor and trailer tandem is generally 75 feet. The travel weight can be approximately 80,000 pounds.

In some embodiments, an area, for example, one hundred sixty feet by 60 feet immediately adjacent to the support pad 300 on both sides is blocked off and reserved to allow for assembly, set-up, and upon conclusion of its use, dismantling of this unit. Access to this area from the adjacent roadway infrastructure preferably be available in all weather conditions, while taking into consideration the weight of the trailer and supporting vehicles.

Exemplary electrical options are provided below. The electrical power for the mobile unit 100 can be 480 volt AC, 3-phase Wye system with neutral and ground, at 200 Amperes. The frequency can be 60+/−2 Hertz. The maximum voltage variance can be +11%/−4% from nominal voltage. The maximum line regulation can be 2.5%. The maximum line-to-line imbalance can be 3%. For power cord/plug, a Russell Stoll 200 Amp plug, can be supplied with the 50 feet power cord for connection to facility power. The cord connection point can be on the roadside of the trailer at around mid-point. For electrical support requited at the facility, a 200 Amp, 480 Volt, 5 wire dedicated service including, for example, a Russell Stoll 200 Amp receptacle, can be mounted in a NEMA 3R rated enclosure to meet local codes requirements. An auxiliary earth ground connection point may be required in addition to the ground circuit within the pin and sleeve connector. An easily accessible NEMA 3R service disconnect in the immediate area is preferable.

The ground for the mobile unit 100 can be, for example, originated at the system power source, e.g., transformer or first access point of power into a facility, and be continuous to the system power disconnect on the mobile trailer 120. This ground can be spliced with high compression fittings and can be terminated at each distribution panel it passes through. When it is broken for a connection to a panel, it can be connected into an approved grounding block with the incoming and outgoing ground in this same grounding block, which then can be connected to the steel panel. The connection at the power source can be at the grounding point of the neutral—ground if a Wye transformer is used. In the case of an external facility, it can be bonded to the facility ground point at the service entrance.

In some embodiments, the ground wire can generally be copper wire with a minimum AWG 1/0 or the same size as the power feeders, whichever is larger. This means that if there is a primary feeder to a distribution panel of 500 MCM with a secondary feeder to this system of AWG 1/0 wire, the ground to the distribution panel can be 500 MCM with an AWG 1/0 to the system. The ground wire impedance from the system disconnect, including the ground rod, preferably not have an impedance greater than 2 ohms to earth as measured by one of the applicable techniques, for example, ANSI/IEEE Standard 142-1982.

In some embodiments, a 15 feet ground cable can be pre-installed and can be found in the forward most, entry door side of the mobile trailer. In some embodiments, a grounding rod is provided and installed as part of the system installation.

When the mobile unit 100 is generating radiation for either imaging or treatment, an exclusion zone is generally required to prevent exposure to either radiation workers or members of the public. This exclusion zone is generally determined based on the level of radiation exposure and local, state and federal requirements. It is possible to add shielding that allows a building to be closer, but the distances allowed may be determined by the customer's physicist and local, state and federal requirements.

FIGS. 13-18 depict diagrams of exemplary radiation scatter and leakage measurements conducted on the mobile unit 100 of FIG. 1. In some embodiments, measurements can be acquired by using a PTW Unidos E electrometer and a PTW TK-30 large volume chamber. Measurements can be engaged at different field sizes (FS) and gantry angles (G). Leakage measurements can be engaged with the multileaf collimator completely closed (or field size of 0 cm×0 cm). Full scatter measurements can be produced with the collimator in the full open position (or 28 cm×28 cm). All measurements can be displayed as a percentage of the delivered dose at isocenter. All displayed data are at the level of isocenter and radiate out at 1 m increments at various angles from zero degrees to 360 degrees.

Based on the exemplary measurements and calculations, expected radiation exposure results for the mobile unit 100 are provided in this disclosure and the above-mentioned distances are exemplary recommendations. The final site plan may also be determined based on distances to adjacent buildings and structures. In addition, as with the installation of any ionizing radiation device, the appropriate site radiation survey should be conducted to verify compliance with these recommendations. Failure to correctly calculate and construct the radiation barriers and shielding as required may result in radiation exposure levels that are in excess of allowable limits, and may present hazards to radiation workers and members of the public.

In some embodiments, 6-10 anchoring points embedded in the support pad 300 are provided. In some embodiments, it is preferable that a minimum of 6 anchor points be used. See FIG. 12 for a typical pad layout and typical tie down. Actual thickness of the support pad 300 can be based on, for example, site conditions, coach weight distribution, and other factors. More or less anchoring points can optionally be used.

A typical LINAC system uses a 6 MV FFF beam. The maximum dose rate can be 800 cGy/min. The maximum treatment field can be 28 cm×28 cm. The isocenter can be 100 cm. The unit can employ a beam stop so that the primary consideration for shielding is leakage and scatter. A typical LINAC system can deliver 3D, IMRT, and VMAT treatments.

Shielding considerations for the mobile radiation oncology coach system 10 can have the following exemplary assumptions: workload, use factors (U=1), occupancy times, design goal (permissible limits), distances, and utilization rate (beam on time). These considerations allow many variants to the external shielding design of the mobile radiation oncology coach system 10. Design goals for unrestricted areas can be set as 1 mSv/yr (0.02 mSv/wk). Design goals for restricted areas can be set as 5 mSv/yr (0.10 mSv/wk). The conventional exposure rate in any one hour of 2 mR/hr guideline can be used. In addition, occupancy factors and utilization rate can be considered. In addition, actual instantaneous dose rates may optionally be considered as well.

The following lists an exemplary series of iso-scatter/leakage measurements (see FIGS. 13-18) for calculating shielding requirements. As a guideline, the following parameters were used to calculate the required shielding.

| Parameters | Value |
| --- | --- |
| Workload | 1,200,000 mGy/wk (based on a workload of 40 patients per day) |
| Use Factor | 1.0 (leakage and scatter) |
| Occupancy | Based on location |
| Distances | Measured in meters with 0.3 meter from barrier |
| Design Goal | 1 mSv/year (unrestricted), 5 mSv/year (restricted) |
| IMRT | 4 (used for workload leakage) |

Figure 3:
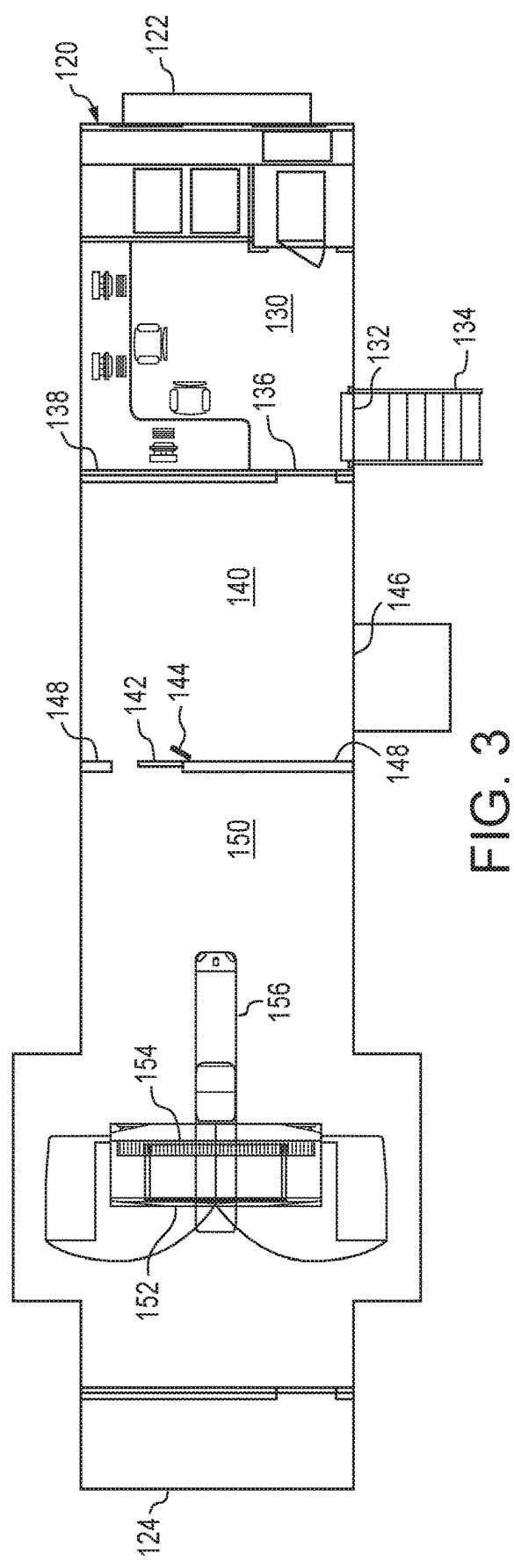
FIG. 3 is a top view of the trailer of the mobile unit illustrated in FIG. 1. The trailer illustrated in FIG. 3 is in a clinic mode.
Figure 4:
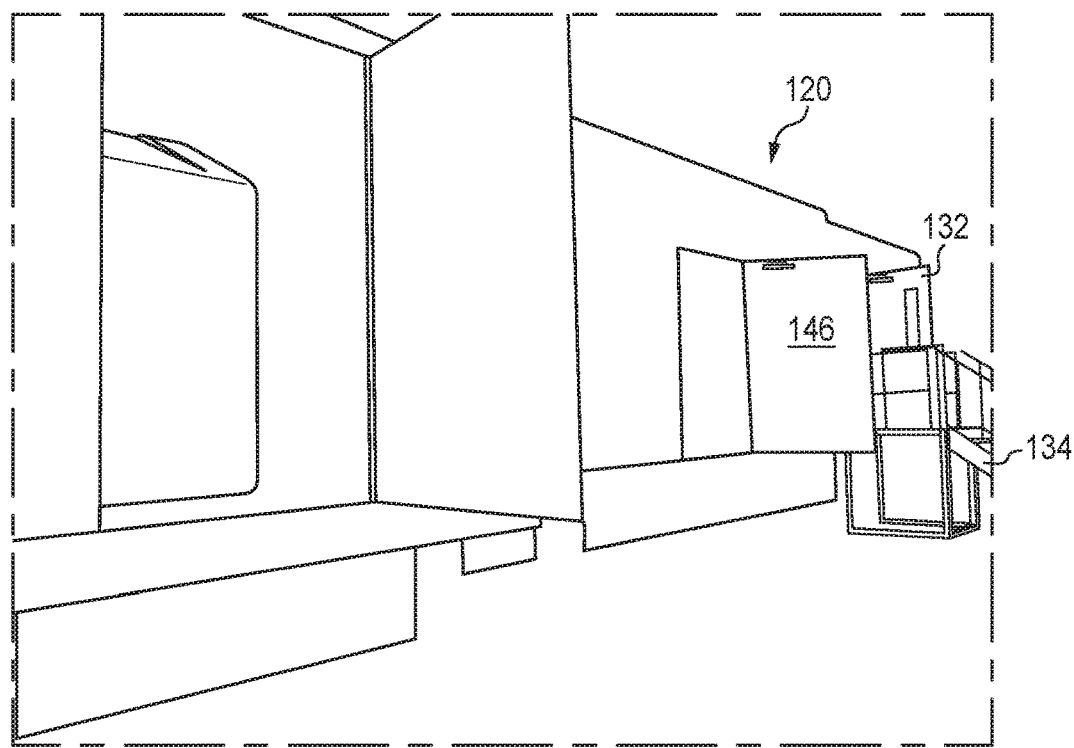
FIG. 4 depicts a partial rear-left perspective view of the trailer with an entry door and a primary entrance door open.

Referring to FIGS. 2-3, the mobile trailer 120 has a front end 122 and a rear end 124. Between the front end 122 and rear end 124, the interior space of the coach 120 can be partitioned into multiple rooms. In some embodiments, as shown in FIGS. 2-3, the coach 120 includes a control console room or area 130, a vestibule 140, and a treatment room or area 150. As shown in FIGS. 2-3, the treatment room 150 is closer to the rear end 124 than the vestibule 140 and the control console room 130 while the vestibule 140 is closer to the rear end 124 than the control console room 130. In some embodiments, other partitions or arrangements for the rooms/areas 130, 140, 150 can be provided. For example, in some embodiments, only the treatment room 150 and control console area 130 are partitioned. In other embodiments, only the treatment room 150 is provided in the coach 120 and the functions of the control console room can be provided outside of the coach 120 via, for example, wired or wireless communications.

In some embodiments, the control console room 130 can contain the operator's station and the planning station. The control console room 130 can also be an entry room and has a front door 132 for entering and exiting the coach 120. A stair 134 can be provided to facilitate the access. In some embodiments, the control console area 130 has an access door 136 for connecting the control console area 130 and the vestibule 140.

In some embodiments, a door 142, for example a sliding door, is provided for connecting the vestibule 140 and the treatment room 150. The sliding door 142 can slide into wall 148. The sliding door 142 can be loaded with lead bricks to form a pocket door. In one embodiment, the pocket door 142 can weight about 5000 lbs.

Figure 8B:
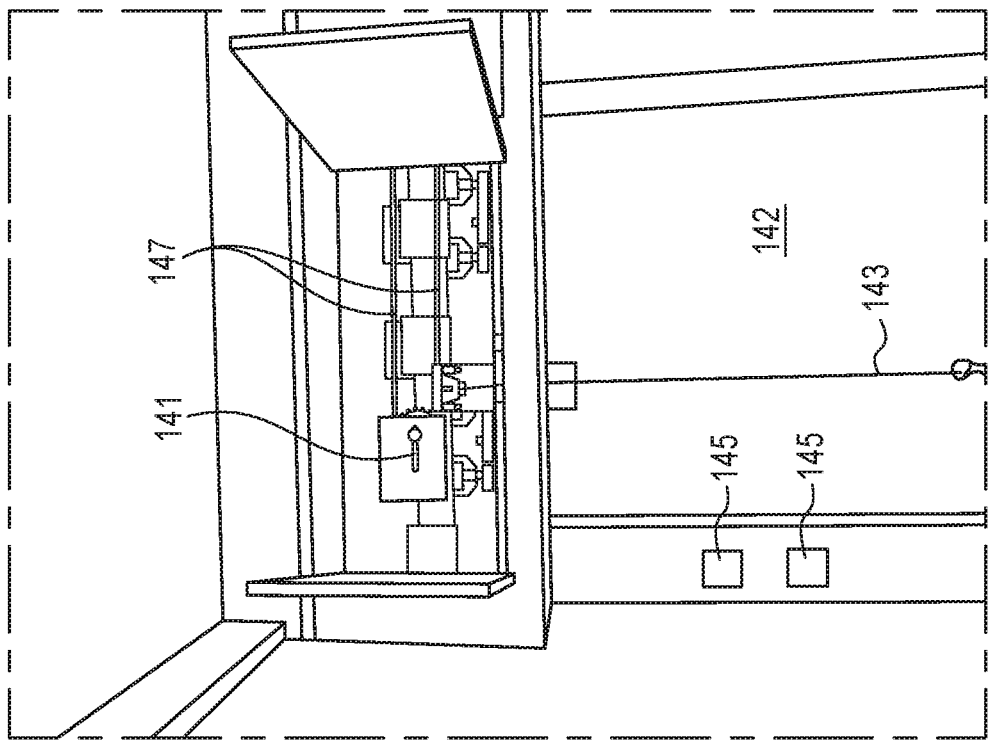
FIG. 8B depicts a perspective view of a pocket door of FIG. 8A with the cabinet door open to show a motor for driving the pocket door.
Figure 8A:
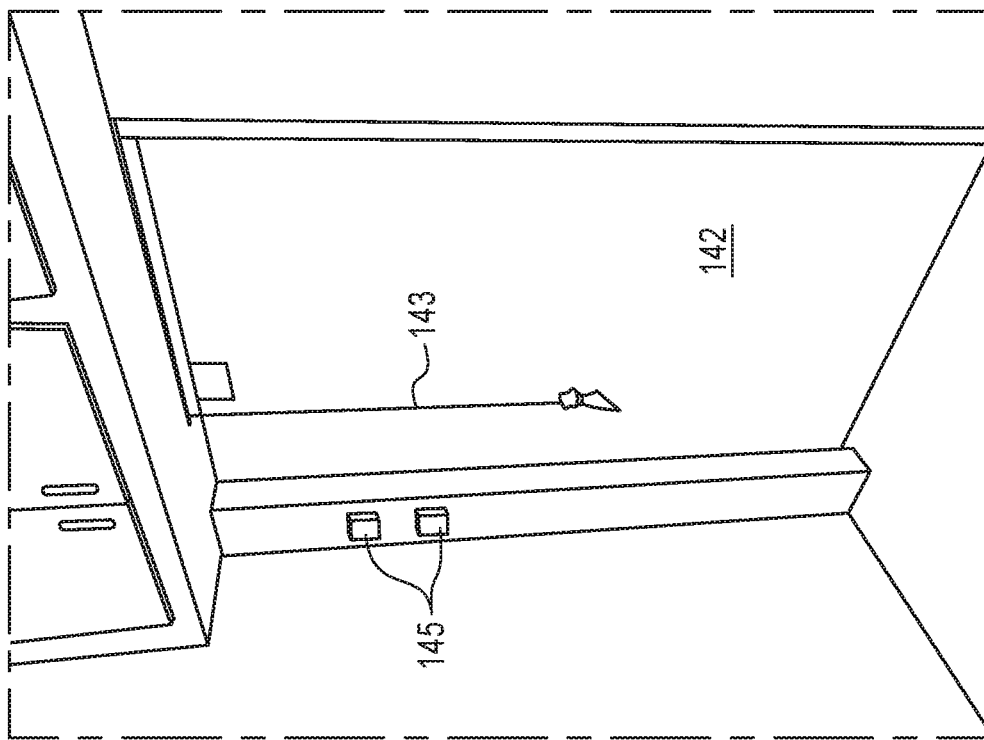
FIG. 8A depicts a perspective view from the treatment room of a pocket door with a cabinet door closed.
Figure 8C:
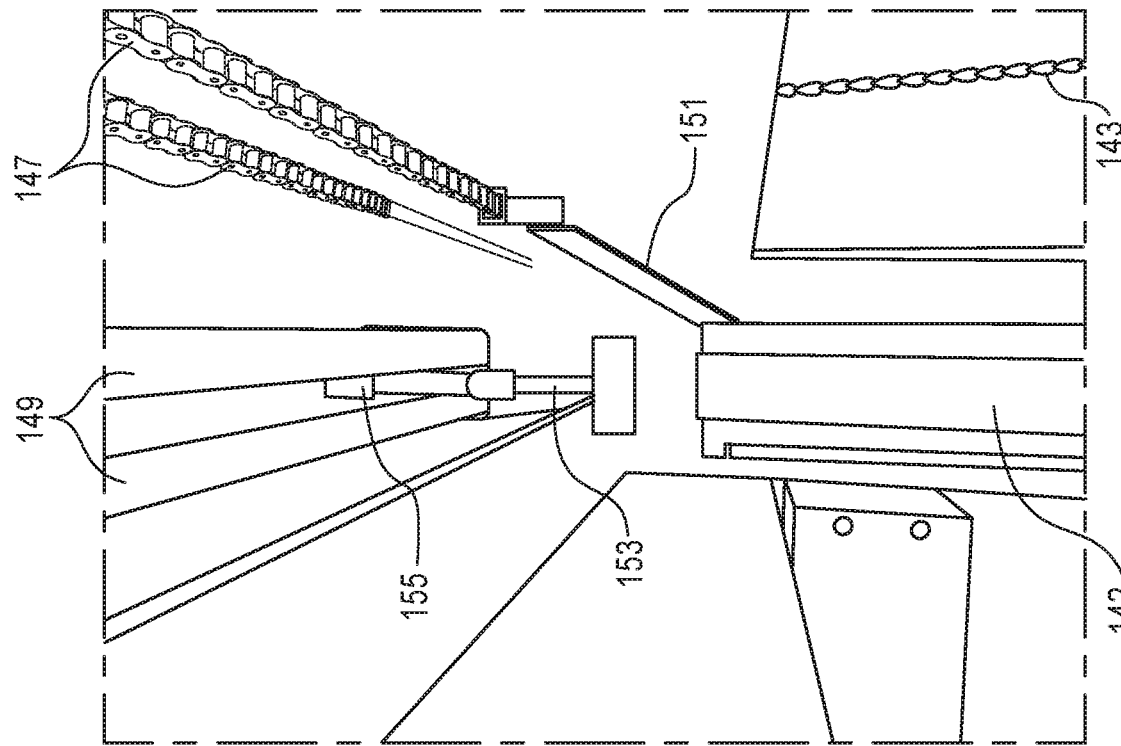
FIG. 8C depicts a perspective view of a pocket door of FIG. 8A with the pocket door open to show the engagement mechanism, top trail and wheel.

Referring also to FIGS. 8A-8C, in some embodiments, through an engagement mechanism 151, the sliding door 142 can be mechanically driven by a drive chain 147 that is engaged with a motor 141. The motor 141 can be controlled by door switches 145 from the treatment room 150 and switches (not shown) from the vestibule 140. A track or rail 149 can be installed at an upper location of the sliding door 142 to accept one or more wheels 155 that are coupled to the sliding door 142 through a supporting mechanism 153. Additional wheels can be provided at the bottom of the sliding door 142 to facilitate the sliding of the door 142 on a bottom track or rail provided on the floor between the vestibule 140 and the treatment room 150. In one embodiment, the track or rail is provided as recessed in the floor about ½ inches.

A lever 143 can be provided for manually disengaging the sliding door 142 and the motor 141 so that and the sliding door 142 can be open/close manually from the treatment room 150, for example, in case of an emergency.

Figure 9:
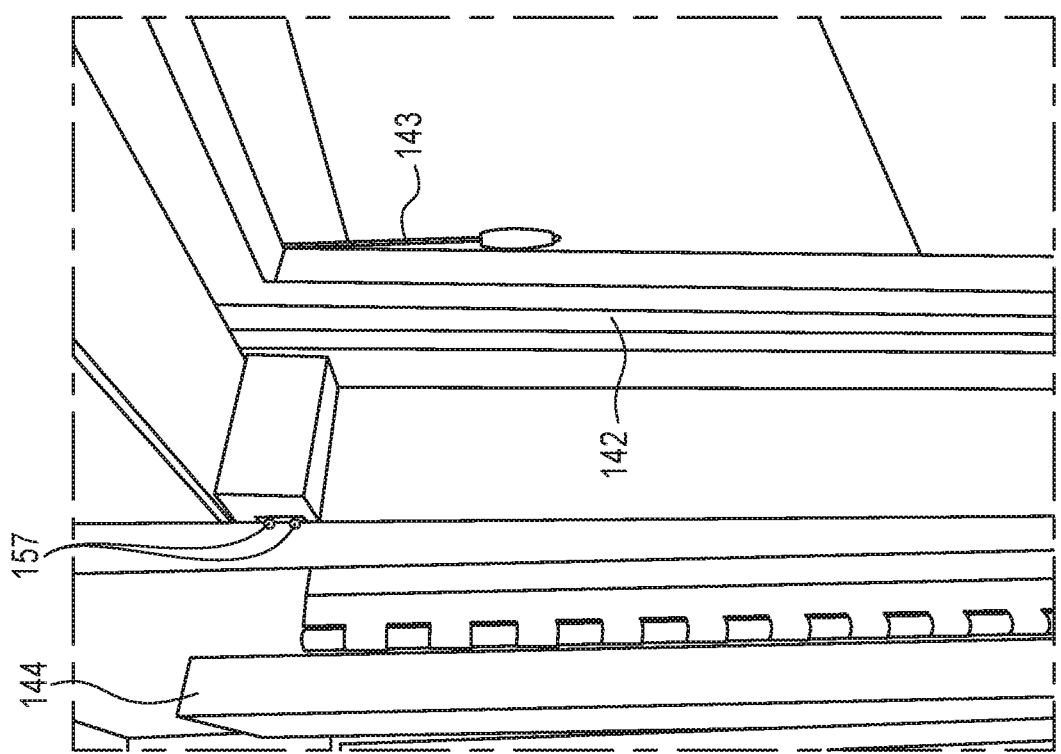
FIG. 9 depicts a perspective view from the vestibule to show a box for interlock switches.

Referring also to FIG. 9, in some embodiments, the vestibule 140 has a swing door 144 which is preferably closed for the treatment to be delivered. One or more interlock switches 157 can be installed for redundancy and fail safe to insure the swing door 144 is shut during treatment delivery.

The vestibule 140 can be provided with a door 146 that can be used as the primary entrance or for use with the wheelchair lift.

A patient under treatment can also enter the coach 120 from the front door 132. After confirmed by a representative of the control console room 130, the patient can enter the vestibule 140 through the access door 136. Then the patient can be guided to the treatment room 150 for treatment through the pocket door 142.

In some embodiments, the treatment room 150 can be designed for installation of a LINAC system 152 or other treatment or diagnostic instrument(s). A LINAC system 152 generally uses microwave technology to accelerate electrons in a wave guide and enable these electrons to collide with a heavy metal target to produce high-energy x-rays. These high energy x-rays can be shaped as they exit the machine to conform to the shape of the patient's tumor, enabling the customized beam can be directed to the patient's tumor. The x-ray beam comes out of a part of the accelerator called a gantry 154, which can be rotated around the patient. Radiation can be delivered to the tumor from many angles by rotating the gantry 154 and moving the treatment couch 156.

Figure 5:
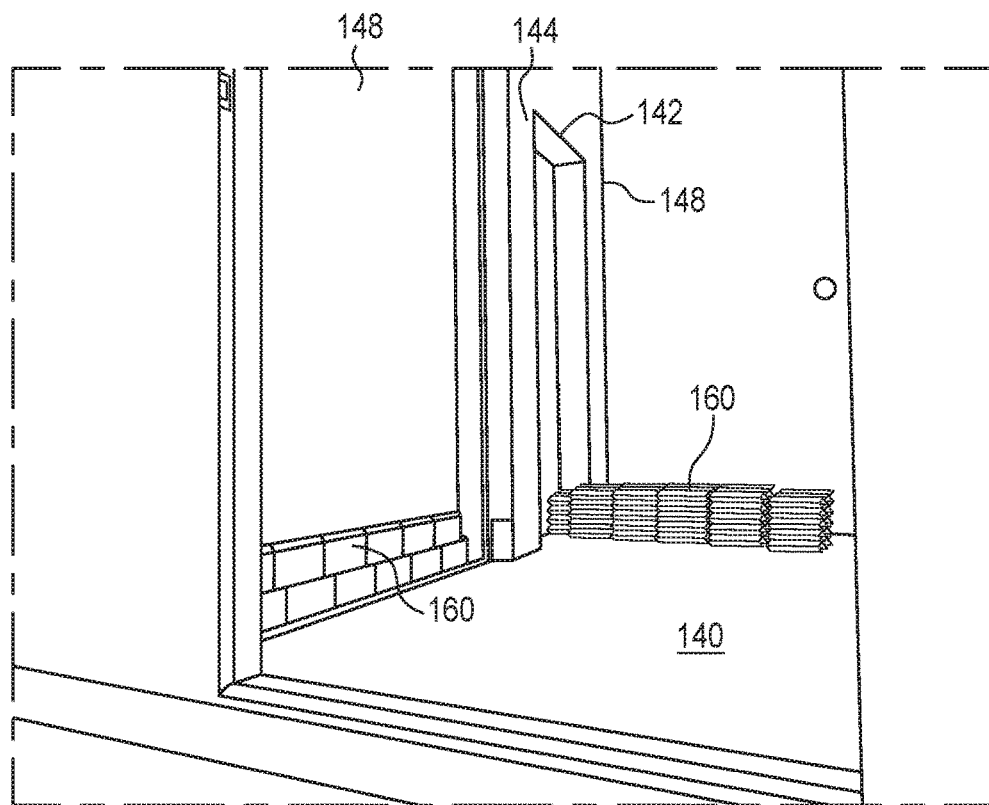
FIG. 5 depicts a partial front-left perspective view of the trailer with a door open to show the vestibule with the internal shielding under installation. The door leading into the vestibule area can be used as the primary entrance or for use with the wheelchair lift.
Figure 7:
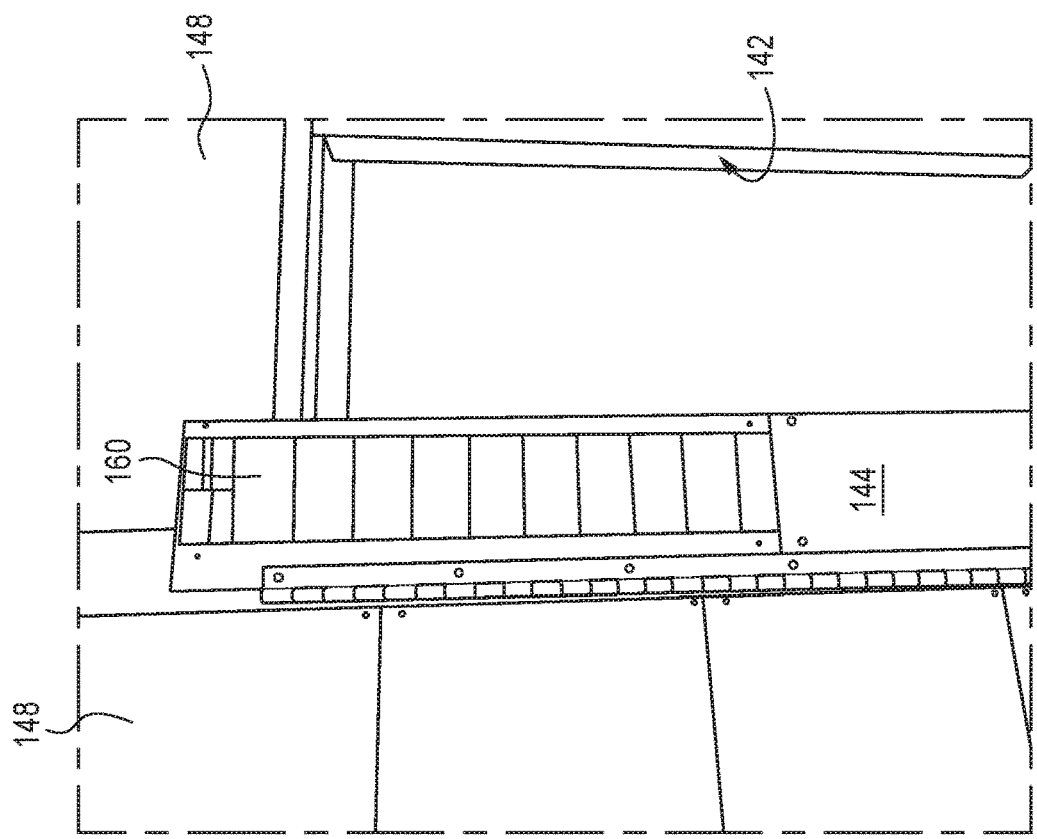
FIG. 7 depicts a perspective view of a swing door of the vestibule with the internal shielding under installation.
Figure 6:
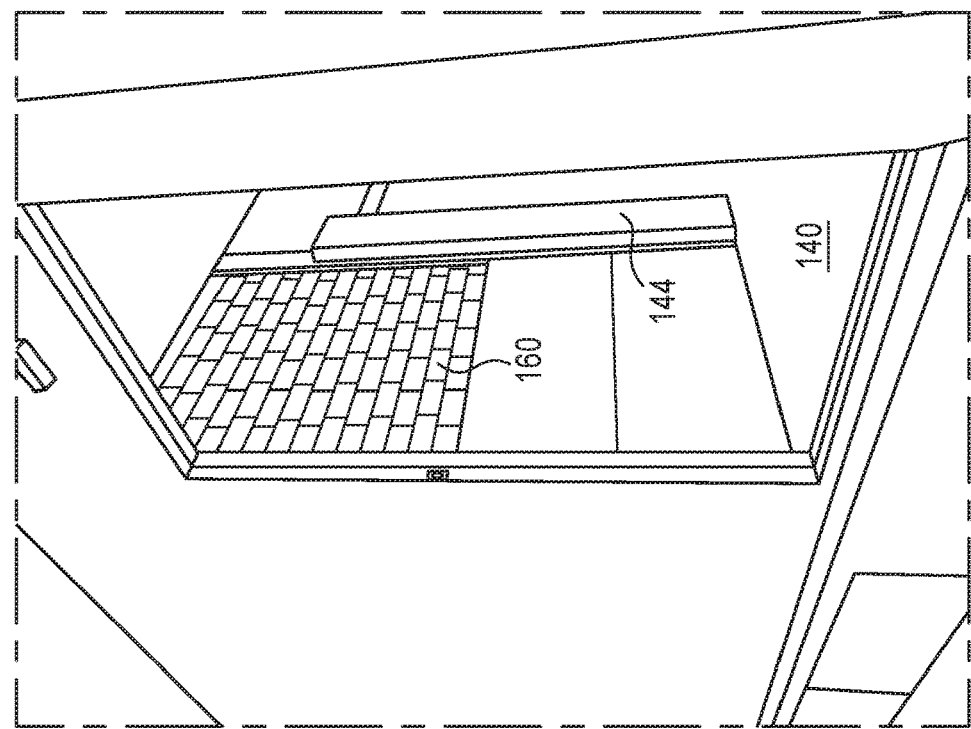
FIG. 6 depicts another partial front-left perspective view of the trailer with the primary entrance door open to show the vestibule with the internal shielding under installation.

Because radiation may scatter or leak from the treatment room 150 during a patient's treatment, protection to people outside of the treatment room 150 is desired. In some embodiments, the coach 120 can have shielding for protecting the control console area 130 during treatment operations. In some embodiments, lead (Pb) shielding 160, for example interlocked lead bricks, is used in walls 138, 148 and doors 142, 144 to block line of site of leakage and scatter. In other embodiments, standard shielding materials can be used. The wall 138 between the vestibule 140 and the control console room 130 can provide secondary or additional shielding for protecting the control console area 130. Referring to FIGS. 5-7, internal lead shielding formed by interlocked lead bricks 160 is applied to the wall 148 and doors 142, 144.

The actual thickness of the interior walls and doors are determined based on standard techniques. In some embodiments, using standard lead (Pb) shielding materials, the thickness of lead bricks on the interior wall 138 between the control console room 130 and the vestibule 140 is 2 inches, the thickness of lead bricks on the interior wall 148 between the vestibule 140 and the treatment room 150 is 4 inches, the thickness of lead bricks on the pocket door is 2 inches, and the thickness of lead bricks on the swing door is 2 inches. In some embodiments, the access door 136 between the control console room 130 and the vestibule 140 can be made without shielding and is there for privacy purposes only. Alternatively, the access door 136 can be provided with shielding if necessary. In some embodiments, different thicknesses of the shielding can be used based on different shielding materials and/or radiation scatter and/or leakage.

In some embodiments, the pocket door 142 between the vestibule 140 and the treatment room 150 can be a steel door with 2 inches of lead bricks. The steel plates holding the lead in place can be ¼ inches steel or ½ inches steel.

In some embodiments, the coach 120 advantageously incorporates alternating doors between the treatment room 150, vestibule 140 and control console room 130 to provide effective shielding. For example, a manual swing door 144 can be added. The manual swing door 144 can contain 2 inches of interlocked lead bricks 160 to take away any potentially not blocked direct line of sight of the machine 154 and those located in the console area. In some embodiments, non-manual or automated doors may optionally be used.

In some embodiments, the internal shielding 160 is installed after the trailer 120 has arrived at a designated site. In this configuration, the mobile unit 100 can meet the highway weight limitations set forth by the state authorities. A forklift (not shown) may be utilized to unload the lead shielding 160 (and other accessories) from a secondary vehicle. If a forklift is needed, a site survey may be conducted to determine the size of the forklift prior to the trailer's arrival. Alternatively, the internal shielding 160 is installed before the trailer 120 arrives at the designated site. In this configuration, the mobile unit 100 can be ready for used in a timely manner.

In some embodiments, coach 120 is equipped with limited yet adequate internal shielding 160 so as to achieve energy efficiency for relocation of the coach 120 to a designated site. The protection of the public external to the coach 120 is achieved using external shielding provided on the outside of the coach 120.

In some embodiments, concrete or high-density concrete for the external shielding is used surrounding the coach 120. The amount of external shielding required can be dependent on, for example, one or more or all of the following factors: workload, distance to surrounding areas, occupancy of surrounding areas, height of surrounding buildings, density of concrete used for shielding, and/or barrier location. The external shielding may be customized and does not need to be symmetric depending on the above listed parameters. The closer the coach 120 is placed to an existing occupied structure, the more shielding will generally be required.

In some typical examples, the mobile radiation oncology coach system workload stays fairly constant (35-40 patients per day). The radiation decreases by $1/R^2$, where R is the distance from the radiation source. In other words, when the distance from the radiation source is doubled, the radiation exposure decreases by approximately ¼. Occupancy Rate (T) can be determined by how often someone will be in a certain area. If people are in an area 100% of the time (T=1) the machine is on, then that area must be shielded as needed/appropriately. If a person is in an area where there is little to no occupancy and no direct line of sight to the particle accelerator, in theory, that area would not need as much shielding. If there are multi-story structures, then that can be taken into account as well in determining the appropriate shielding.

In some embodiments, the following external shielding recommendation is based on the following:

| Parameters | Value |
| --- | --- |
| Design Goal | 0.02 mGy/wk (unrestricted) |
| Workload | 1,200,000 mGy/wk |
| Leakage | 0.05% |

| Parameters | Value |
| --- | --- |
| Occupancy Rate | T = 0.5 and T = 1.0 |
| Shielding | High-Density Concrete (240 pcf) |

On leakage parameter, Federal regulations require that radiation producing machines cannot exceed 0.1% of the output at 1 meter from the radiation source. Many existing machines are able to achieve 0.05% of the calibrated output at 1 meter. From the measurements depicted in FIGS. 13-18, the leakage parameter may be even less than 0.05%.

For the shielding parameter, in some embodiments, concrete of around 147 pcf is used to achieve more cost effective result for adequate shielding.

Figure 10:
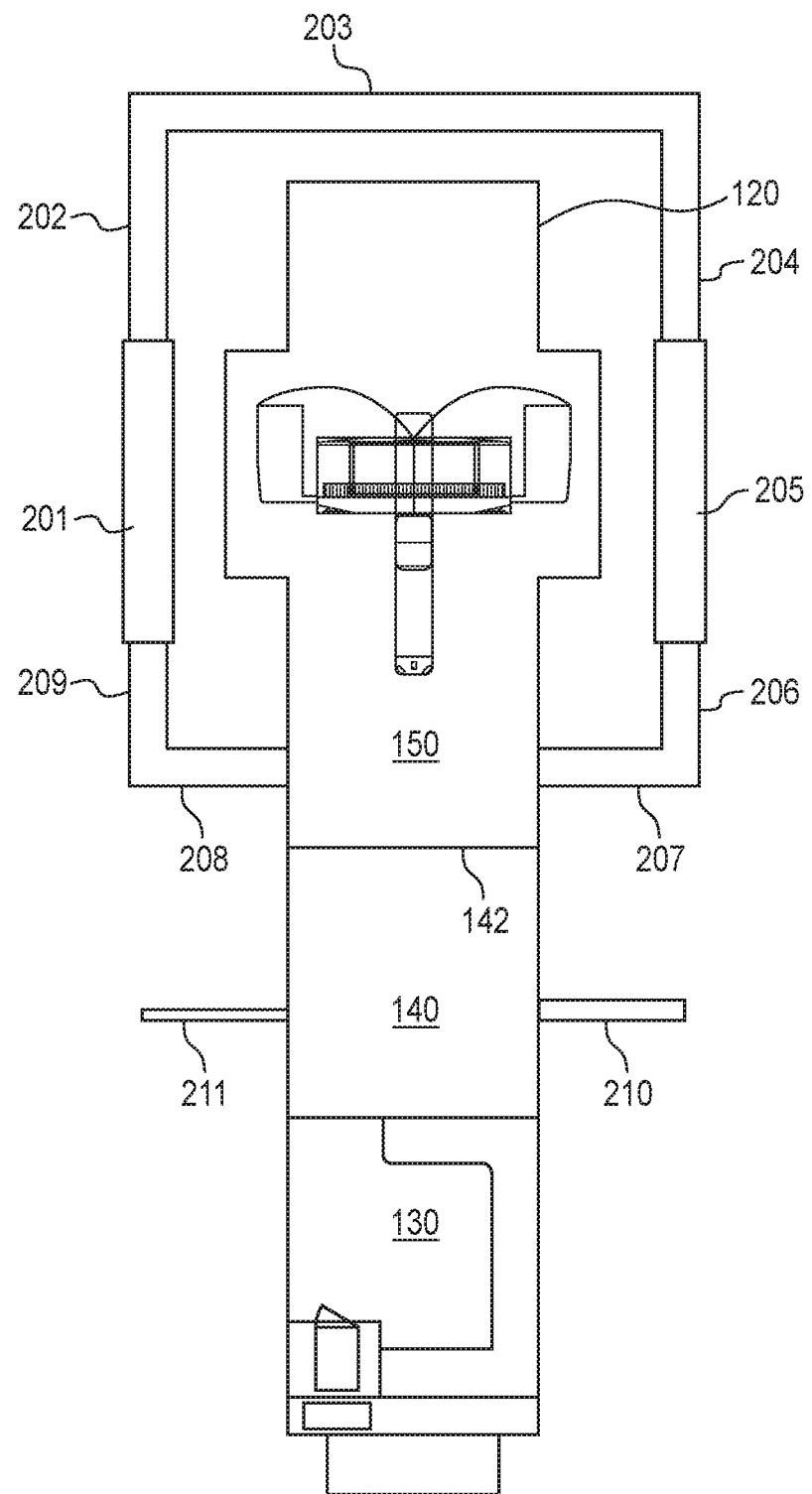
FIG. 10 is a top view of the trailer of the mobile unit illustrated in FIG. 1 with external shielding. The trailer illustrated in FIG. 10 is in a clinic mode.

FIG. 10 depicts a top view of the trailer 120 of the mobile unit 100 illustrated in FIG. 1, with external shielding barrier 201-211 positioned according to some embodiments. The trailer or coach 120 illustrated in FIG. 10 is in a clinic mode. As shown in FIG. 10, each of the external shielding barriers or walls 201-211 is placed at a calculated and/or predetermined distance from the nearest surface of coach 120. In some embodiments, the calculated distance is 3 meters. In some embodiments, at least 1 meter is disposed between the furthest out wall and the shielding to account for room to maneuver around the unit when parked.

FIG. 11 is table showing exemplary recommended thickness (in inches, when Occupancy Rate T=0.5 and T=1.0, respectively) for each external shielding barrier 201-211 identified in FIG. 10.

As depicted in FIG. 11, barrier 210 is thicker than barrier 211 although both barrier 210 and barrier 211 are placed on relatively symmetrical positions. In consideration of the position of the pocket door 142, it is preferable to have the barrier 210 thick enough to prevent or reduce any potential radiation leaked through the pocket door 142 or the surrounding of the pocket door 142. In other embodiments, barrier 210 and barrier 211 can have the same thickness or other thicknesses.

The height of the external shielding walls 201-211 is dependent on location of nearby structures. This will be different on each location the unit is placed. The height of the external barriers 201-211 is configured to block a direct line of sight of the leakage coming from any gantry position. Alternative thicknesses, heights and/or materials may optionally be used to accomplish similar shielding results.

In the present embodiment, the ceiling of coach 120 is not shielded. Alternatively, the coach 120 can also include shielding in the ceiling. This may help to reduce the shielding height and thickness of the external shielding barriers 201-211. Skyshine can be evaluated as needed.

In the present embodiment, shielding below the trailer 120 is not required for lateral barriers and for the rear of the trailer 120. The external barriers 201-211 will block any ground scatter. Alternatively, shielding below the trailer between the tractor 110 and the control console area 130 can be provided. In some embodiments, sand is used to provide such shielding. The amount of sand can be range from 30" to 36".

In some embodiments, external shielding 201-211 may require using L-block shields where the external shield abuts with the trailer 120. This is to ensure there are no areas of leakage.

The x-ray radiation generated by the mobile unit 100 is typically 6 MV. It is typically when about 10 MV that pair production is achieved and elements become radioactive. As concrete is a low Z-element, even at high energy levels, advantageously no radioactive material is created. Accordingly, all external shielding barriers 201-211 will not be contaminated after used. In some embodiments, external shielding barriers 201-211 can be removed from site after use and can be reused.

A full radiation survey can be conducted around the trailer 120 after installation. Any areas that exceed limits for unrestricted areas will be marked as restricted areas. These areas may not be occupied by members of the general public, and any professionals working in these areas may be permitted based on training and being equipped with the appropriate monitoring badge (personal monitor). Areas that have no occupancy may require little to no shielding. These areas can preferably be treated as restricted and access to these areas may be limited. Fences and appropriate signage may be required. These areas are preferably monitored closely by the staff and security.

It is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions/processes to those described herein insofar as they do not depart from the spirit and scope of the present invention.

For example, the specific sequence of any described component and/or process may be altered. For example, certain processes are conducted in parallel or independent, with other processes, to the extent that the processes are not dependent upon each other. Other alterations or modifications of the above components and/or processes are also contemplated. For example, further insubstantial changes to the components, systems and/or processes are also considered within the scope of the processes described herein.

In addition, features illustrated or described as part of one embodiment can be used on other embodiments to yield a still further embodiment. Additionally, certain features may be interchanged with similar devices or features which perform the same or similar functions. It is therefore intended that such modifications and variations are included within the totality of the present invention.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional. By use of the term "at least one of A and B" herein, it is intended to mean "one or more of X and/or Y."

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

The detailed description, for purposes of explanation, used specific nomenclature to provide a thorough understanding of the invention. However, it will be apparent to one skilled in the art that specific details are not required in order to practice the invention. Thus, the detailed descriptions of specific embodiments of the invention are presented for purposes of illustration and description. They are not intended to be exhaustive or to limit the invention to the precise forms disclosed. Modifications and variations of the above detailed description are considered within the scope of the described invention. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

What is claimed is:

1. A mobile radiation oncology coach system comprising:
    a trailer configured to include a control console area and a treatment area, the treatment area being equipped with a medical treatment facility that can emit radiation;
    internal shielding disposed between the control console area and the treatment area; and
    external shielding provided at a predetermined location outside of the trailer.

2. The mobile radiation oncology coach system of claim 1, wherein said internal shielding comprises interlocked lead bricks.

3. The mobile radiation oncology coach system of claim 2, wherein the interlocked lead bricks comprises a predetermined thickness to provide substantially effective shielding between the control console area and the treatment area.

4. The mobile radiation oncology coach system of claim 2, wherein the plurality of barriers are made of concrete.

5. The mobile radiation oncology coach system of claim 1 further comprising:
    a vestibule area located between the control console area and the treatment room; and
    a second internal shielding provided between the vestibule area and the control console area.

6. The mobile radiation oncology coach system of claim 5, wherein the second internal shielding comprises additional interlocked lead bricks comprising a second thickness to provide substantially effective shielding between the control console area and the vestibule area.

7. The mobile radiation oncology coach system of claim 5 further comprising:
    a first door configured and providing access between the treatment area and the vestibule area, the first door including first shielding; and
    a second door configured and providing access between the vestibule area and the control console area, the second door is further configured to be constructed near an opposite side of said trailer, preventing a direct line of sight between the treatment area and the control console area.

8. The mobile radiation oncology coach system of claim 1 further comprising:
    an alternating door between the treatment room and the control console area, wherein the alternating door contains interlocked lead bricks to shield direct line of sight of the medical treatment facility and people located in the control console area.

9. The mobile radiation oncology coach system of claim 1 further comprising:
    a first door configured and providing access between the treatment area and the control console area, the first door including first supplemental shielding.

10. The mobile radiation oncology coach system of claim 9, wherein the first door is further configured to be constructed and positioned to prevent a direct line of sight between the treatment area and the control console area.

11. The mobile radiation oncology coach system of claim 9, further comprising:
    a swing door including a second supplemental shielding, and constructed and positioned to shield radiation that may be emitted in an area associated with the first door between the treatment area and the control console area.

12. The mobile radiation oncology coach system of claim 1, wherein the medical treatment facility includes medical linear particle accelerator (LINAC).

13. The mobile radiation oncology coach system of claim 1, wherein the external shielding comprising a plurality of barriers.

14. The mobile radiation oncology coach system of claim 1 further comprising a support pad dimensioned to support the trailer, and wherein the support pad comprises concrete.

15. The mobile radiation oncology coach system of claim 1 further comprising a tractor, and wherein said tractor and said trailer are arranged in tandem.

16. The mobile radiation oncology coach system of claim 1, wherein said external shielding is configured to be a predetermined distance and separate from said internal shielding.

17. The mobile radiation oncology coach system of claim 1, wherein an amount required for said external shielding is dependent on one or more of the following factors: workload, distance to surrounding areas, occupancy of surrounding areas, height of surrounding buildings, density of said external shielding, or location of said external shielding.

18. The mobile radiation oncology coach system of claim 1, wherein a height of said external shielding is configured to block a direct line of sight of the leakage coming from any gantry position.

19. The mobile radiation oncology coach system of claim 1, wherein said external shielding blocks any ground scatter from the rear of the trailer.

20. The mobile radiation oncology coach system of claim 1, wherein said external shielding is removable from the site after use.

21. The mobile radiation oncology coach system of claim 1, wherein said external shielding is provided at a predetermined location outside and around a predetermined area of the trailer.

22. A method for providing a mobile radiation oncology services, the method comprising:
    moving a trailer to a designated site, the trailer having a control console area and a treatment area being equipped with a medical treatment facility that can emit radiation;
    providing an internal shielding disposed between the control console area and the treatment area; and providing an external shielding at a predetermined location outside of the trailer.

23. The method of claim 22, wherein the internal shielding comprising interlocked lead bricks.

24. The method of claim 22 further comprising:
providing an alternating door positioned between the treatment area and the control console area, wherein the alternating door contains interlocked lead bricks to take away direct line of sight of the medical treatment facility and people located in the control console area.

25. The method of claim 22, wherein the medical treatment facility is a LINAC.

26. The method of claim 22, wherein the external shielding comprising a plurality of barriers.

27. The method of claim 26, wherein the plurality of barriers is made of concrete.

28. The method of claim 22 further comprising:
providing a support pad dimensioned to support the trailer, wherein the support pad is made of concrete.

29. The method of claim 22 further comprising:
providing a tractor, wherein the tractor and the trailer are arranged in tandem.

30. The method of claim 22 further comprising:
securing the trailer after the trailer is moved to the designated site.

31. The method of claim 22 further comprising:
removing the external shielding after the services is complete.

32. The method of claim 22, said external shielding are not moving with the trailer.

* * * * *